United States Patent [19]

Watson et al.

[11] Patent Number: 4,815,473

[45] Date of Patent: * Mar. 28, 1989

[54] METHOD AND APPARATUS FOR MONITORING RESPIRATION

[75] Inventors: Herman L. Watson, Perrine; Marvin A. Sackner, Miami Beach, both of Fla.; Frank D. Stott, Oxford, England

[73] Assignee: Respitrace Corporation, Miami Beach, Fla.

[*] Notice: The portion of the term of this patent subsequent to Jan. 5, 1999 has been disclaimed.

[21] Appl. No.: 120,211

[22] Filed: Nov. 6, 1987

Related U.S. Application Data

[63] Continuation of Ser. No. 14,133, Jan. 29, 1987, abandoned, which is a continuation of Ser. No. 858,100, Apr. 30, 1986, abandoned, which is a continuation of Ser. No. 705,396, Feb. 25, 1985, abandoned, which is a continuation of Ser. No. 263,722, May 14, 1981, abandoned, which is a continuation of Ser. No. 102,408, Dec. 11, 1979, Pat. No. 4,308,872, which is a continuation of Ser. No. 893,023, Apr. 3, 1978, abandoned.

[30] Foreign Application Priority Data

Apr. 7, 1977 [GB] United Kingdom ................. 7714783

[51] Int. Cl.$^4$ ............................................. A61B 5/08
[52] U.S. Cl. ................................................... 128/721
[58] Field of Search ............................. 128/721–724, 128/774, 715; 324/71.1

[56] References Cited

U.S. PATENT DOCUMENTS

| | | | |
|---|---|---|---|
| 2,649,573 | 8/1953 | Goldberg et al. | 324/71.1 |
| 3,142,796 | 7/1964 | Goldberg et al. | 324/71 |
| 3,340,867 | 9/1967 | Kubicek et al. | 128/693 |
| 3,407,818 | 10/1968 | Costanzo | 128/384 |
| 3,483,681 | 12/1969 | Tiep | 128/721 |
| 3,560,845 | 2/1971 | Goldberg et al. | 324/34 |
| 3,731,184 | 5/1973 | Goldberg et al. | 73/194 EM X |
| 4,036,215 | 7/1977 | Doll | 73/194 EM X |
| 4,137,910 | 2/1979 | Murphy | 128/713 X |
| 4,308,872 | 1/1982 | Watson et al. | 128/721 X |
| 4,433,693 | 2/1984 | Hochstein | 128/721 |

FOREIGN PATENT DOCUMENTS

| | | | |
|---|---|---|---|
| 40-15437 | 6/1965 | Japan | 128/721 |
| 652453 | 3/1979 | U.S.S.R. | 73/730 |
| 1178121 | 1/1970 | United Kingdom | 73/172 |
| 1350113 | 4/1974 | United Kingdom | 324/200 |

OTHER PUBLICATIONS

Milledge, J. S. et al., "Inductive Plethysmography-A New Respiratory Transducer", Proc. of the Physiol. Soc., Jan. 1977, pp. 4–5.

Konno, K. et al., "Measurement of Separate Volume Changes of Rib Cage & Abdomen During Breathing", Jrnl. Appl. Phys., vol. 22, pp. 407–422, publ. 1967.

"Pulmonary Ventilation Measured from Body Surface Movements", Science, vol. 156, pp. 1383–1384, 1967.

Gilbert et al., "Breathing Pattern during $CO_2$ Inhalation Obtained from Motion of the Chest and Abdomen", Resp. Physiology, vol. 13, pp. 238–252, publ. 1971.

Ashutosh et al., "Impedance Pneumograph and Magnetometer Methods for Monitoring Tidal Volume", Jrnl. Appl. Physiology, vol. 37, No. 6, pp. 964–966, publ. 1974.

Shapiro and Cohen, The Use of Mercury Capillary Length Gauges, etc., 1965, pp. 643–649, Transactions of the New York Academy of Sciences.

Primary Examiner—Francis J. Jaworski
Attorney, Agent, or Firm—Schechter, Brucker & Pavane

[57] ABSTRACT

A method and apparatus are shown for monitoring respiration volumes by continuously measuring, while the patient breathes, variations in the patient's chest cross sectional area, or preferably, variations in both chest and abdomen areas. Each area is measured by measuring the inductance of an extensible electrical conductor closely looped around the body, by connecting the loop as the inductance in a variable frequency LC oscillator followed by a frequency-to-voltage converter and a voltage display. Calibration is made by measuring the area variations for a few breaths while directly measuring corresponding volumes of breath, preferably while the patient assumes at least two body positions, for example sitting and supine. The method and apparatus may also be used to monitor changes in area of any non-magnetic object.

20 Claims, 6 Drawing Sheets

METHOD AND APPARATUS FOR MONITORING RESPIRATION

This is a continuation, of U.S. application Ser. No. 014,133, filed Jan. 29, 1987, now abandoned, which is a continuation of U.S. application Ser. No. 858,100, filed Apr. 30, 1986, and now abandoned, which is a continuation of U.S. application Ser. No. 705,396, filed Feb. 25, 1985, and now abandoned which is a continuation of U.S. application Ser. 263,722, filed May 14, 1981, and now abandoned, which is a continuation of U.S. application Ser. No. 102,408, filed Dec. 11, 1979, and now U.S. Pat. No. 4,308,872 which is a continuation of U.S. application Ser. No. 893,023 filed Apr. 3, 1978 and now abandoned.

BACKGROUND OF THE INVENTION

This invention relates to a method and apparatus for continuously monitoring the respiration of patients, particularly critically ill patients in intensive care units.

Most methods used in the past involve the use of face masks or mouthpieces, which is not only invasive and discomforting to the patient, but also disturbs the very breathing patterns being measured. These prior art methods may require cooperation from the patient, impossible if the patient is critically ill or perhaps comatose, and mouthpieces certainly may not be left in place for continuous monitoring. Other prior art methods which are less disturbing for the patient and his breathing pattern, such as use of a pneumograph, are incapable of providing data of sufficient accuracy for clinical use.

One prior art approach measured changes in the thickness of the chest by placing coils on the front and back, sending an alternating current through one coil, and detecting the voltage induced in the other coil. The equipment used was somewhat bulky, and the linear changes in chest thickness did not represent breathing volumes very well. It did have the advantage of not requiring face masks or mouthpieces, however.

SUMMARY OF THE INVENTION

The above and other shortcomings in prior art measurement of respiration are overcome by applicants' discovery that clinically accurate data on breathing volumes can be derived from continuous measurements of the cross sectional areas of the upper chest and the lower abdomen, and that each of these areas can be measured by measuring the inductance of an extensible conductor looped about the torso at each location.

The volume of a breath is equal to a corresponding change in the compartmental volume of the torso when that breath is taken. Further, this change in compartmental volume has been found to be fairly accurately represented by a corresponding change in the cross sectional area of the chest during that breath, which can be measured. If the patient remains in one body position, such as sitting, there will be a fixed proportion between measured area change and volume of breath. However, if the patient stands up, or lies down prone, this fixed proportion changes, and must be found all over again for each new body position.

Applicant has found a way to avoid the necessity of calibrating area change to breath volume for each and every body position. Two measurements of cross sectional area change are preferably used, one for the upper chest, the other for the lower abdomen. Then, if a ratio or relative weighting factor for the importance of chest area change relative to abdomen area change is determined for a given patient, with usable clinical accuracy the compartmental volume change and so respiration volume can be found from the two area changes, properly weighted. One ratio, one weighting factor, has been found to be clinically accurate for all positions assumed by the patient. The ratio can be determined from measurements made in each of any two body positions, and will be good for all positions. One only need measure breathing volume by some direct method, while at the same time measuring the two area changes, for the first position, then repeat the measurements for the second position. The weighting factor and the proper factor to convert to breathing volume are then easily calculated, or can be set by the apparatus in a foolproof calibration step.

To measure the change in cross sectional area, an insulated wire formed to permit body extension is wrapped about and held closely encircling the torso, and its inductance is read out continuously by making this insulated wire loop the inductance in a variable frequency LC oscillator. The oscillator is in turn connected to a frequency-to-voltage converter, which is connected to a scaling amplifier, which in turn is connected to a digital voltmeter.

When two measurements are taken, of both chest and abdomen, the corresponding scaling amplifiers are set during a calibration procedure (mentioned above) to the ratio of relative weight then found, and connected to a summing amplifier, which in turn is connected to a digital voltmeter or other display.

Since changes in area enclosed by a conductor loop result in proportional changes in inductance of that loop, it can be seen that changes in the output display by the digital voltmeter will, after calibration, represent breathing volumes. A recorder can be used with or in place of the digital voltmeter, to provide a fixed record for later analysis.

DETAILED DESCRIPTION OF THE INVENTION

The starting point in the inventive apparatus is an electrically conductive loop which is held closely around a body portion being measured. Changes in the area enclosed by this loop result in proportional changes in the inductance of the loop, a property which is measured and displayed by circuits and apparatus to be described later. The extensible conductor is formed preferably by affixing the conductor to an extensible carrier as will be described below.

The preferred carrier for holding the conductive loop closely about a body portion is a tubular stretch bandage, as described, for example, in U.S. Pat. Nos. 3,279,465 and 3,307,546, both granted to V. Cherio et al, the disclosures of which are incorporated by reference in their entireties. These tubular bandages may be obtained in the form of a garment similar to a pullover sweater, or in tubes of any desired diameter and length in sizes to fit any portion of the anatomy. They are knitted in a relatively open pattern permitting free passage of perspiration, and are soft and freely stretchable, and so are comfortable to wear and permit free movement.

The electrically conductive loop is formed preferably from insulated multi-stranded wire of small gauge, shaped and attached to the tubular bandage in such a way as not to appreciably change the wearing comfort and free movement permitted by the bandage. Similarly, any electronic circuit modules used with the loop and mounted on the bandage are kept small and placed where they will be least obtrusive.

Figure 1:
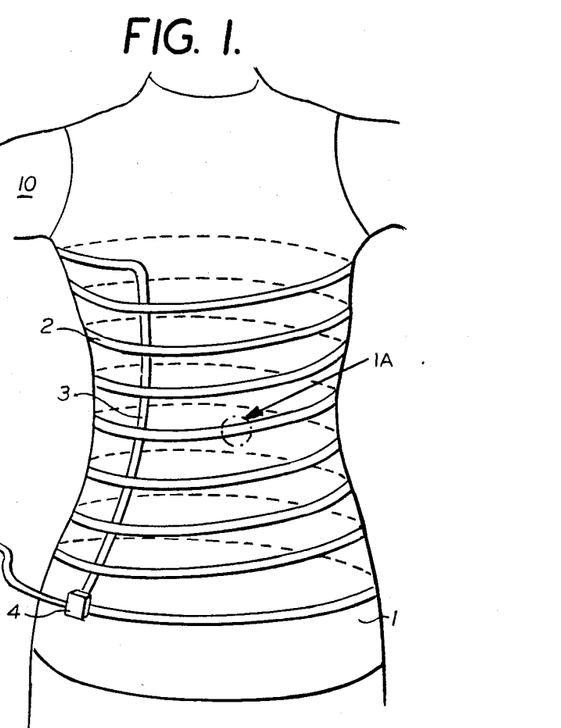
FIG. 1 illustrates an extensible electrical conductor loop attached to a tubular stretch bandage in the form of a sleeveless sweater worn by the patient so the loop is held in close encirclement about the patient's torso while the patient breathes.

FIG. 1 shows a tubular stretch bandage in the form of a long sleeveless sweater 1, worn closely fitted over the torso of a human being 10. Here the conductor 2 has been attached to the sweater in a number of turns around the torso from the lower abdomen to the upper chest, and so will provide a measure of area averaged over the entire torso. More turns may be placed over one portion of the torso and fewer over other portions, if it is desired to give greater weight to changes in area of one portion of the torso relative to others. This multiturn loop is closed by a vertical section 3 returning to the starting point. Both ends of the loop are electrically connected to an electronic circuit module 4, to be described later, which is shown by way of illustration to be placed at the starting point, on the patient's lower right side. A small cable 23, comprised of insulated wires 5, 6 and 7 and ground wire 0, is shown leading away from the circuit module 4, for electrical connection to the rest of the electronic circuitry, described later.

There are a number of alternate ways of forming the conductor 2 and attaching it to the fabric of the tubular stretch bandage 1. As can be seen in the enlarged view of FIG. 1A, the fabric is comprised of heavier, inelastic yarns running generally vertically, and lighter, elastic yarns which follow a zig-zag pattern between the inelastic yarns. The electrical conductor is formed in alternating up and down looplets advancing in a plane. It is attached to the fabric of bandage 1 at points of crossing of the inelastic yarns, by stitches 8 of elastic thread tied to the inelastic yarns.

Figure 1A:
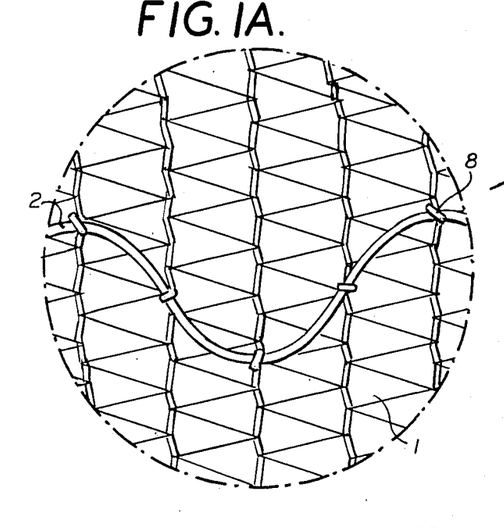
FIG. 1A is an enlarged view showing how the extensible electrical conductor is formed from insulated wire in alternating looplets advancing in a plane to permit extension during breathing, and is attached to the tubular stretch bandage by stitches.
Figure 1B:
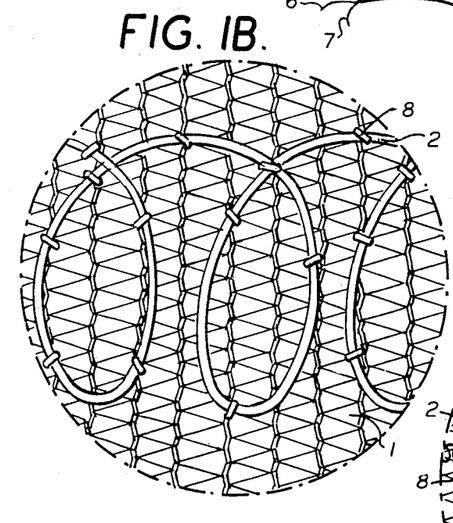
FIG. 1B is an enlarged view which shows the insulated wire formed in planar advancing looplets.
Figure 1C:
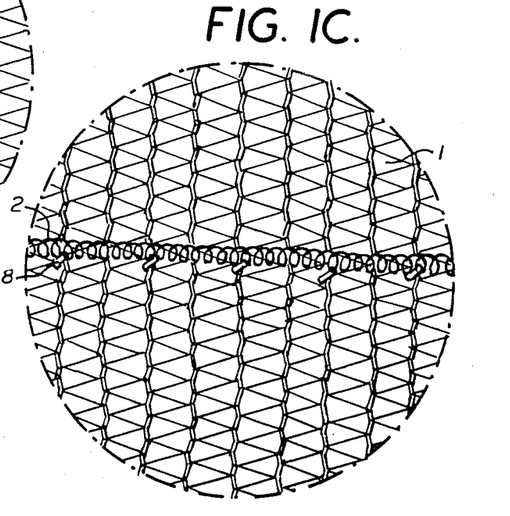
FIG. 1C is an enlarged view which shows the insulated wire formed in an advancing three-dimensional coil.

FIG. 1B shows an alternate forming of the conductor 2 into planar advancing looplets, the bandage 1 and the method of attachment thereto by stitches 8 being the same as in FIG. 1A. FIG. 1C shows yet another alternate form of conductor 2, in a small three dimensional advancing coil, again with the same bandage 1 and the same attachment to the inelastic yarns of the fabric of the bandage by stitches 8 of elastic thread.

Figures 2, 2A, 2D, 2E:
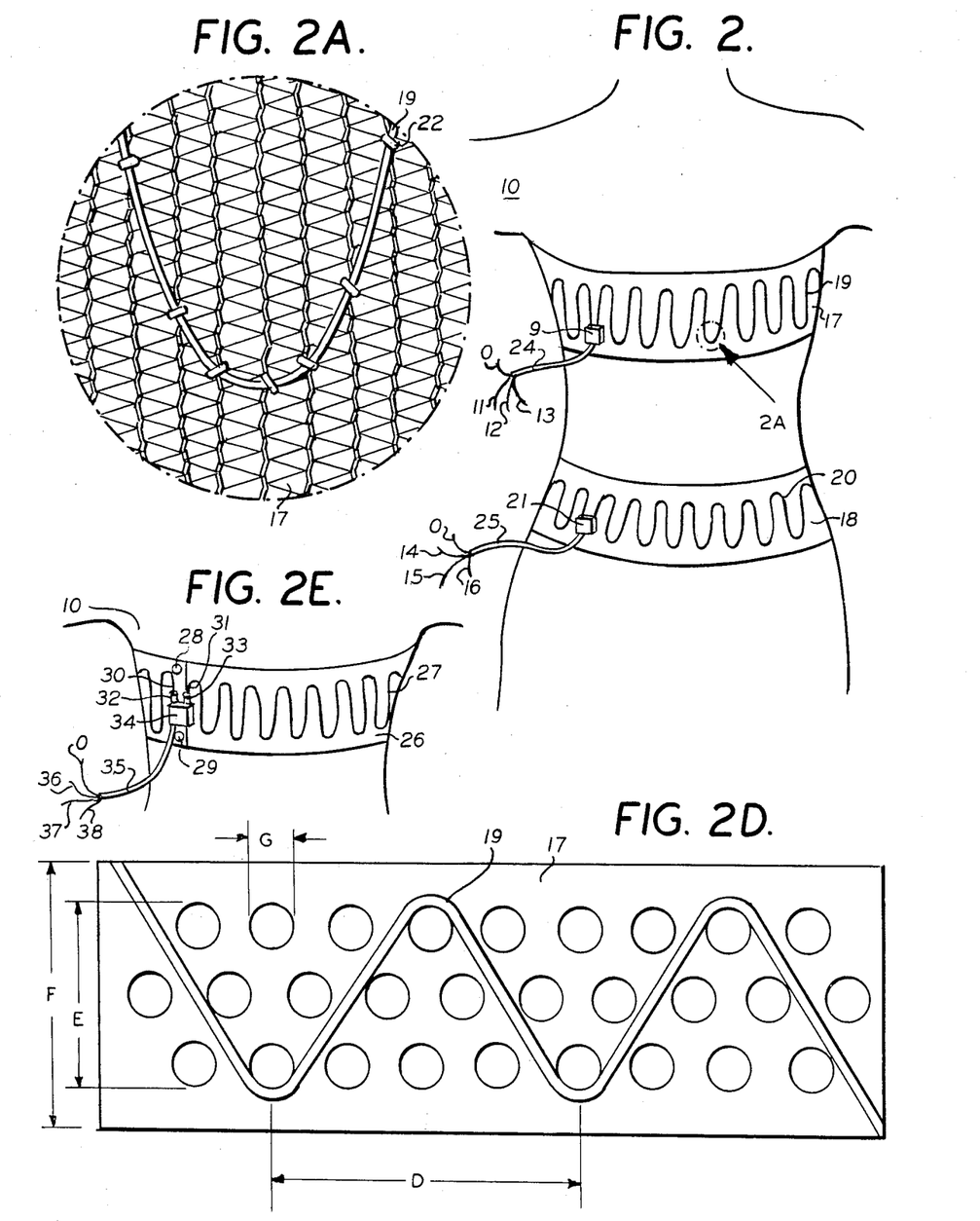
FIG. 2 shows two separate extensible electrical conductor loops attached to elastic tubes in place about the patient's upper chest and lower abdomen.
FIG. 2A is an enlarged view showing the insulated wire attached by stitches to an elastic band which is a tubular stretch bandage.
FIG. 2D shows the insulated wire formed in alternating looplets advancing in a plane and attached to a perforated band of elastomeric material by cementing.
FIG. 2E shows an alternate version of the elastic tube with a conductor mounted, which can be opened like a belt, wrapped about the patient, and fastened together.

FIG. 2 shows a generalized view of the preferred embodiment of the present invention, showing two elastic tubes 17 and 18, in place, respectively, about the upper chest and the lower abdomen of a patient 10. Conductor 19 is mounted in a single turn loop circumferentially of tube 17, and conductor 20 is similarly mounted about tube 18. Conductors 19 and 20 are both formed in advancing up and down looplets advancing in a plane. Tube modules 9 and 21, and cables 24 and 25 extending therefrom and the wires of which they are comprised, are shown in their preferred placement on the patient's right side, and are not discussed further here, being described with the electronic circuitry later.

Alternate embodiments for elastic tubes 17 and 18, for details of the forming of conductors 19 and 20, and for the attachment of conductors 19 and 20 to elastic tubes 17 and 18, are shown in FIGS. 2A, 2B, 2C and 2D, all of which show only elastic tube 17. In each embodiment, elastic tube 18 and its conductor 20 and attachment thereof may be the same as shown for elastic band 17, although it may be any of the variants described, as well.

In FIG. 2A elastic tube 17 is shown as being the preferred tubular stretch bandage. Conductor 19 in this embodiment is stitched to the inelastic yarns of the fabric of the tubular stretch bandage 17 by stitches 22 of elastic thread.

Figure 2B:
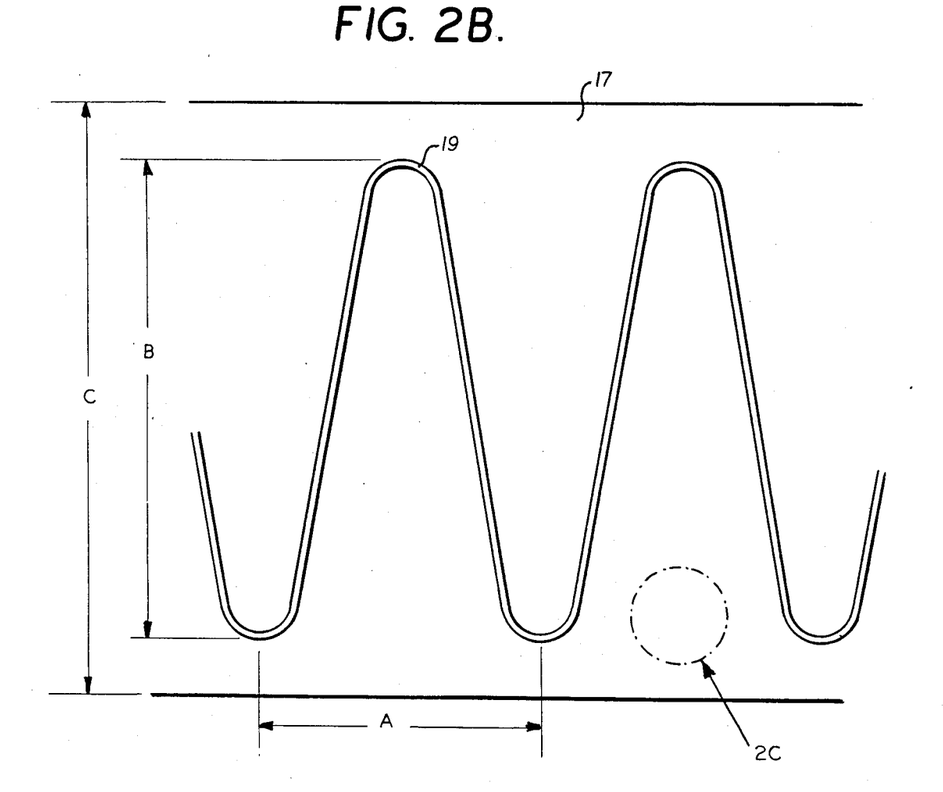
FIG. 2B shows the insulated wire formed in alternating looplets advancing in a plane and attached to a tubular stretch bandage by an adhesive or by heat sealing.
Figure 2C:
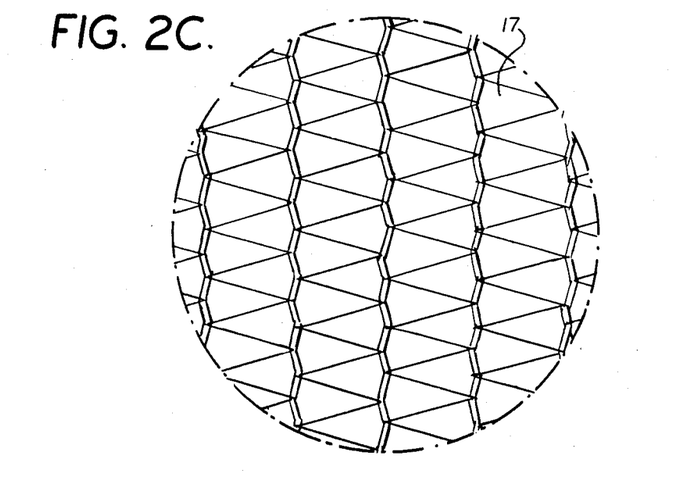
FIG. 2C is an enlarged view of the fabric of the tubular stretch bandage.

The preferred combination of all features of the elastic tubes with mounted conductors is shown in FIGS. 2B and 2C. FIG. 2B shows the preferred geometry of the extensible electrical conductor, formed in alternating up and down looplets advancing in a plane. The pitch A is approximately $2\frac{1}{2}$ inches, the amplitude B approximately $4\frac{1}{2}$ inches, and the width C of the elastic tube approximately $5\frac{1}{2}$ inches. FIG. 2C shows an enlarged view of the fabric of the preferred tubular stretch bandage.

Conductor 19 may be attached to tubular stretch bandage 17 by an adhesive. The preferred attachment is, however, by heat sealing. For this the preferred wire is 28 gauge stranded copper, the preferred insulation is teflon or PVC. The insulated wire is given a precoat of a liquid plastic such as polyurethane, polyamid or polyester chosen for compatibility with the wire insulation and for adequate heat sealed adhesion to the rubbertextile stretch bandage.

The mode of heat sealing may be conventional, and is done with the elastic tube stretched to the chest or abdomen size intended, a variety of sizes being contemplated for the variety of sizes of human beings. The heat sealing may be done one section at a time, depending upon the equipment available, and, similarly, may be done first down the middle of the band, and secondly along the upper and lower sides. The heat cycle time and temperature is a function of the materials chosen, and will be within the ability of persons of ordinary skill. With the material expressly disclosed, each heat seal cycle is between about 10 and 20 seconds, at a temperature sufficient to accomplish adhesion with the precoat employed.

FIG. 2D shows an alternate embodiment, in which tube 17 is made from an elastomeric material such as rubber, to which conductor 19 is cemented with a rubber type cement compatible both with the insulation on the wire and the elastomeric material. To make the tube more comfortable, holes may be provided as, for instance, in the pattern shown and of about $\frac{3}{8}$ inch diameter, so located as not to interfere with the path of the wire, as shown. The looplet pitch D may be approximately $2\frac{3}{4}$ inches, the amplitude E approximately $1\frac{3}{4}54$ inches, and the width F of the tube approximately $3\frac{1}{4}$ inches.

FIG. 2E shows an alternate embodiment of the elastic tube with mounted conductor in which the tube 26 may be opened, as for convenience in placement onto a human torso, and fastened together encircling the torso. Thus, an encircling but openable band is included in the term "tube". Snap fasteners 28 and 29 are shown holding the band together. Any standard fastener means could be used, for example, ribbon ties, hook and eyelet fasteners, Velcro strips, or Ace brand fastener clips for stretch bandages. Any of the band materials described before could be used, with knitted elastic bandage material preferred. Conductor 27 may be formed as described previously, and attached by any of the methods shown before. The ends 30 and 31 of conductor 27 may be fitted with small detachable connector plugs 32 and 33 and module 34 with matching connector sockets (not shown) for electrical connection of the conductor loop to the module. A cable 35 is provided for connecting the module 34 with the rest of the apparatus.

Figure 3:
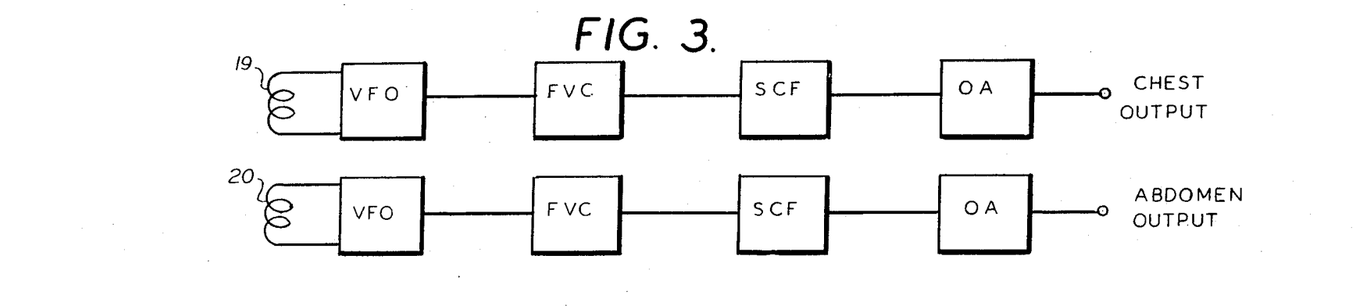
FIG. 3 is a block diagram of apparatus for producing electrical output signals representing chest area and abdomen area.

The starting point having been described, namely a conductive loop closely encircling a body member so that its inductance will be a measure of the cross sectional are encircled, the rest of the respiratory monitoring apparatus will now be considered. The electronics of the respiratory monitoring apparatus can be any circuit that reliably and accurately measures changes in the inductance of the conductive loop mounted on the body encircling tube. Two loops will be provided in the preferred embodiment described in respect to FIG. 2, although a satisfactory, but less sophisticated apparatus can be formed with only one loop. Respiratory movements of the wearer result in changes in the cross-sectional areas and hence in the inductances of the loops. Once these changes in inductance are converted to an electrical signal for each loop, those signals are calibrated by the use the of apparatus described hereinafter to accurately measure the volume of respiration. One apparatus for converting changes in inductance into proportional voltages is shown in FIG. 3 in block diagram form.

A variable frequency oscillator (VFO) is connected electrically to each of the two loops, 19 and 20 in FIG. 2. The resonant frequency of the voltage controlled oscillators is determined by an internal capacitor and the inductance of the conductor loop to which it is attached. This frequency may, for example, be centered at about 1 MHz and varies as the coil it is connected to expands and contracts with respiration. Of course, the term coil is intended to include coils of about one turn as well as a plurality of turns. In the present invention, particular emphasis is placed on the minimization of artifacts caused by movement and on the reduction of parasitic capacitances between the coils and the body of the wearer. This is one reason for preferably placing the oscillator electronics on the garment itself, in modules 9 and 21 in FIG. 2.

The changes in frequency of the variable frequency oscillator are detected and converted to a DC signal by the frequency to voltage converter (FVC) which is fed by the variable frequency oscillator (VFO). The frequency to voltage converter may, for example, consist of a DC restoration circuit and a simple diode detector for conversion of the frequency. The output of the frequency to voltage converter is then connected to a signal conditioning filter (SCF). The lower and higher cutoff frequencies of this filter may, for example, be set for about 0.05 and 10 Hz, respectively. The signal conditioning filter is followed by a voltage amplifier (OA) to boost the output signals to an amplitude of approximately 200 mV peak-to-peak for a one to two liter breathing volume in adults. Thus, as a patient breathes to vary the enclosed are and hence the inductance of coils 19 and 20, the frequency of the signal generated by the oscillator (VFO) will vary in response thereto. This variation will be detected by the frequency to voltage converter (FVC) which will produce a signal, the preferably DC, dependent upon such detected variation of the enclosed area of the torso of the breathing patient. A signal conditioning filter (SCF) "cleans up" this signal, removing unwanted and extraneous high and low frequency components that may have appeared. The output of the signal conditioning filter is then amplified by amplifier OA to provide a signal output of useful magnitude. The output signal may be employed in numerous ways hereinafter described to yield useful information through various types of readouts.

Figure 3A:
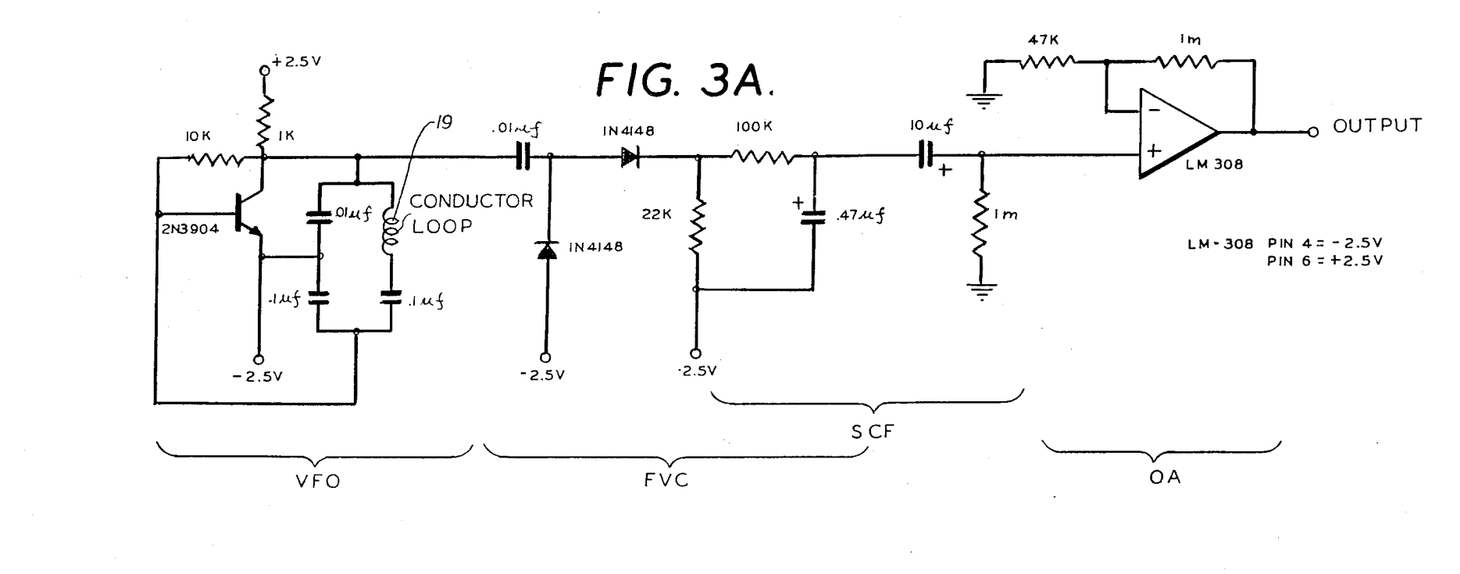
FIG. 3A is a circuit diagram of one embodiment of the apparatus of FIG. 3.
Figure 3B:
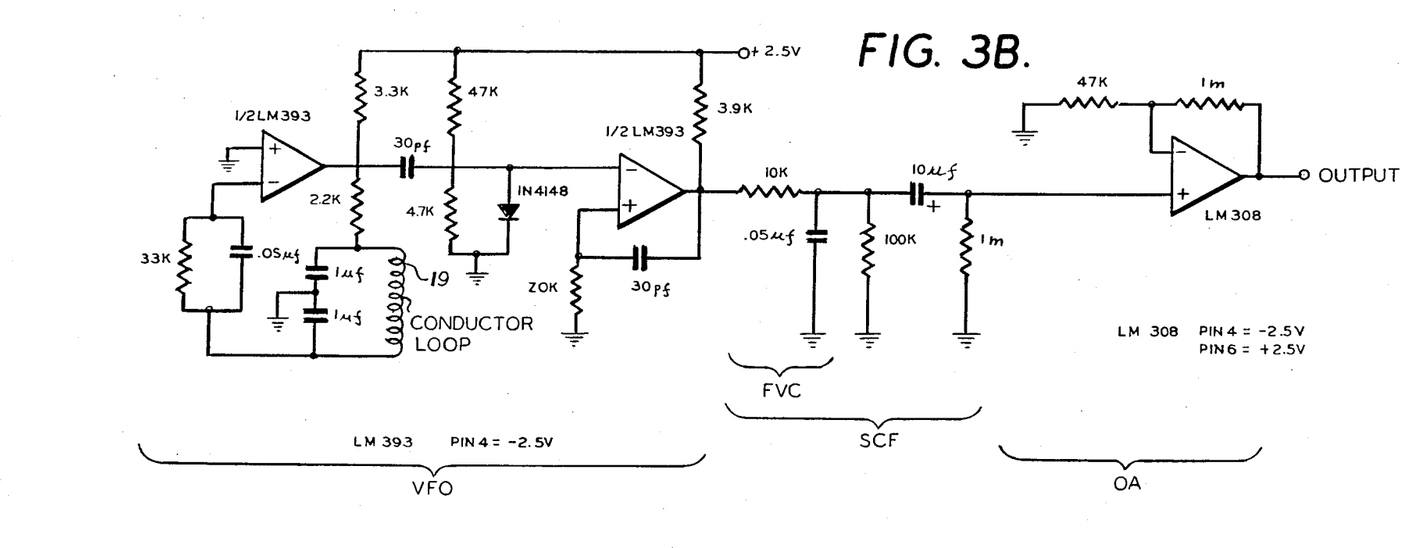
FIG. 3B is a circuit diagram of a second embodiment of the apparatus of FIG. 3.

One skilled in the art can readily select standard circuits to accomplish the functions described for each of these blocks. FIG. 3A shows one such circuit, with brackets below the circuit indicating which portion corresponds to which block. Where it may be purely a matter of nomenclature to decide which portion should be assigned to a given block, overlapping brackets are drawn, indicating that one may assign the overlapping elements to either block as may suit his preferences. FIG. 3B shows an alternate circuit to perform the same function, a preferred embodiment. Typical, and presently preferred circuit elements and values are shown on the drawings and will be readily understandable to a person of ordinary skill. One variation of the circuit shown in FIG. 3B is to combine the chest and abdomen circuits and use one LM399 quad comparator in place of the two LM393 dual comparators (one for each FIG. 3B circuit, ½ at each circuit position indicated) which would be required if there were no such combination. Since the circuits illustrated in FIGS. 3A and 3B are of conventional design, a detailed description of their construction and mode of operation is deemed unnecessary. Numerous variations in this circuitry will readily suggest themselves to persons of ordinary skill and are within the intended scope of this invention.

The circuitry shown in FIG. 3A or in FIG. 3B may be incorporated into one module, such as module 9 in FIG. 2, which would also carry a battery (not shown) to supply the indicated voltages. Preferably, the battery and some part of the circuitry are mounted nearby but not on the tube, in order to keep the module small and of minimum burden to the patient. Thus, in FIG. 3A the module may contain up to and including the second diode IN4148 and not the 22K resistor just to its right. In FIG. 3B, the separation may be just to the left or right of the 100K resistor.

Figures 4, 4A:
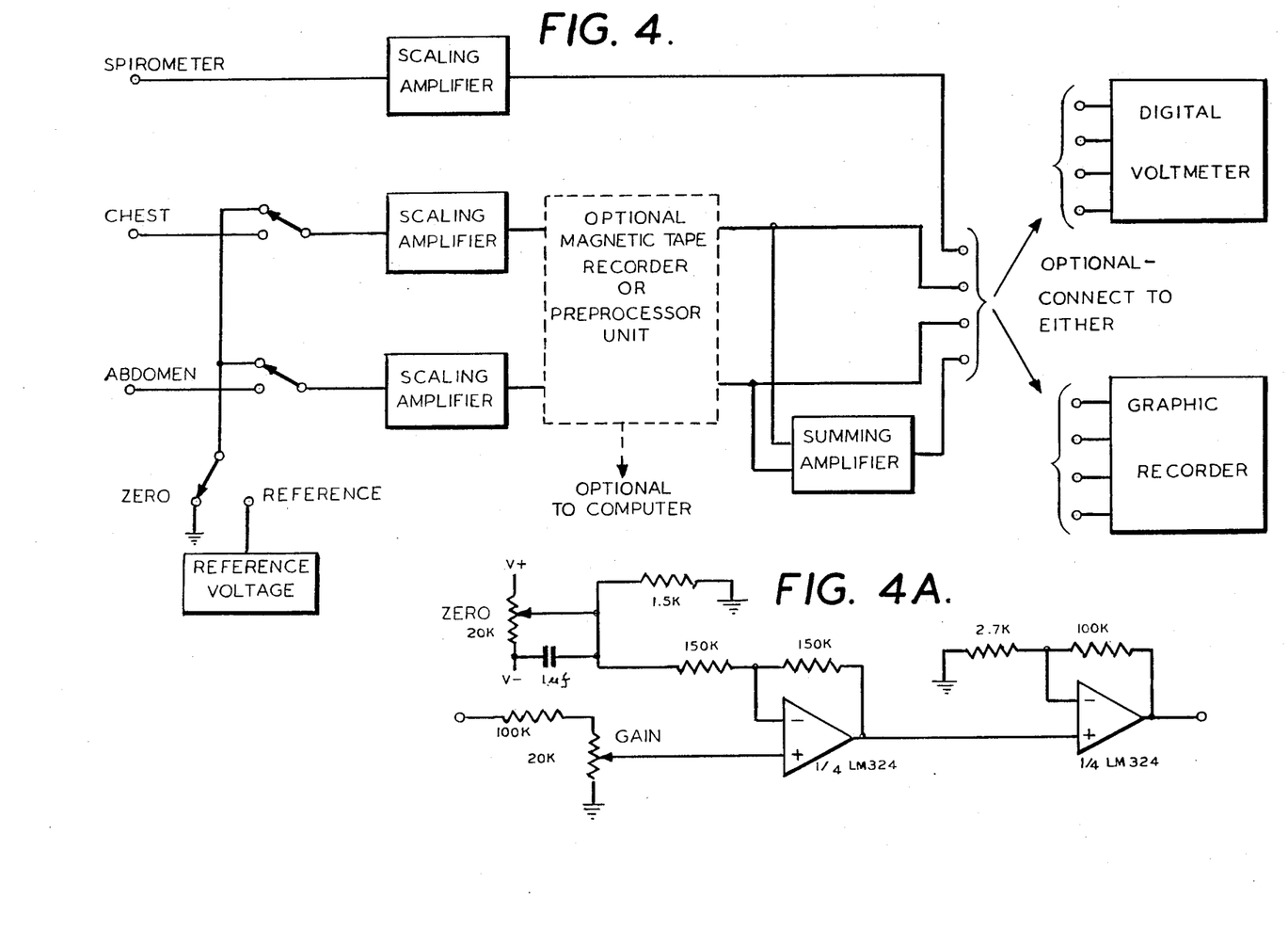
FIG. 4 is a block diagram of an apparatus for receiving electrical signals from the apparatus of FIG. 3 and from a spirometer which directly measures volumes of breath, calibrating and adjusting one relative to the other, summing the chest and abdomen signals, and displaying signals on a digital voltmeter or a graphic recorder. Placement of an optional magnetic tape recorder, or an optional preprocessor unit, is indicated by a dashed box.
FIG. 4A is a circuit diagram of one embodiment of a scaling amplifier for use in the apparatus of FIG. 4.

FIG. 4 shows in block diagram form an apparatus for calibration and operation, which in operation takes the chest output and abdomen output signals from the apparatus of FIG. 3 just described, and converts them to a form useful for one observing a patient's respiration. In addition to terminals for these inputs of the output signals from chest and abdomen circuits of FIG. 3, there is provided an input terminal for a signal from a presently conventional direct respiration measuring apparatus, for example, an Ohio Medical Model 840 spirometer. This conventional apparatus provides a direct measurement of respiration volumes during calibration. A direct current reference voltage source is provided internally as shown in FIG. 4, along with suitable switches, so that during calibration either a zero (electrical ground) signal or a standard reference voltage signal can be substituted for either the chest on the abdomen output from the apparatus of FIG. 3.

A scaling amplifier is shown, next in series, in each of the spirometer, chest, and abdomen signal lines. The purpose of these three scaling amplifiers is, first, to adjust the sizes of the corresponding signals in each line so that they are of a large enough magnitude for convenient use in the equipment that follows, and second, to permit adjustment of each of the three signals to its proper relationship to the other two, during calibration. Calibration will be discussed in some detail below. The adjusted chest and abdomen signals coming from the respective scaling amplifiers are made available directly at two of the four terminals provided for connection to a display apparatus. The spirometer signal, also after adjustment by its scaling amplifier, is made available at a third terminal, and the fourth terminal carries the arithmetic sum of the two adjusted signals for chest and abdomen, the calculation of this sum being done by the summing amplifier shown in FIG. 4. Thus, resulting adjusted signals are all made available to a display, which may be a four channel (or more) graphic recorder, or a digital voltmeter. Examples of each, respectively, are an Electronics for Medicine DR-8 with rapid writer, which records up to eight channels, and an Analogic AN2570 digital voltmeter.

Figure 4B:
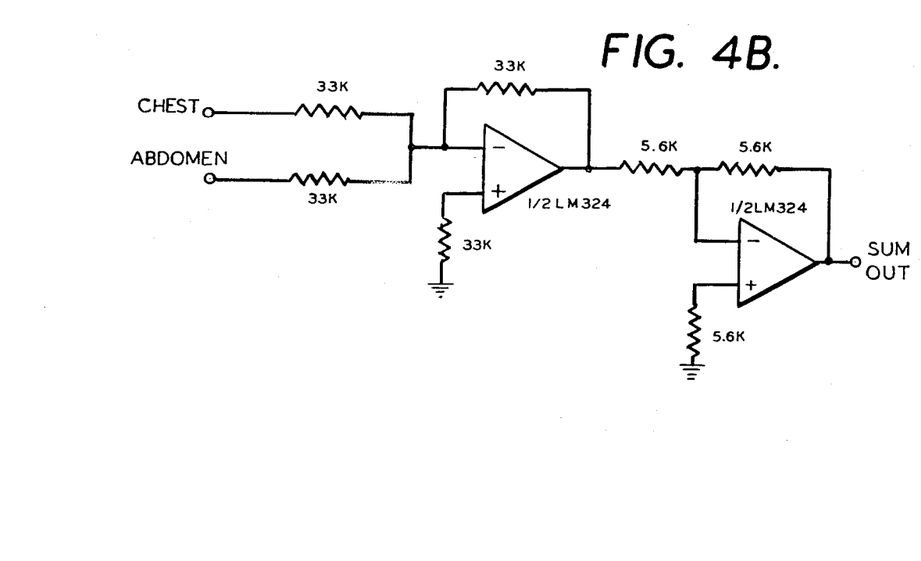
FIG. 4B is a circuit diagram of one embodiment of a summing amplifier for use in the apparatus of FIG. 4.
Figure 4C:
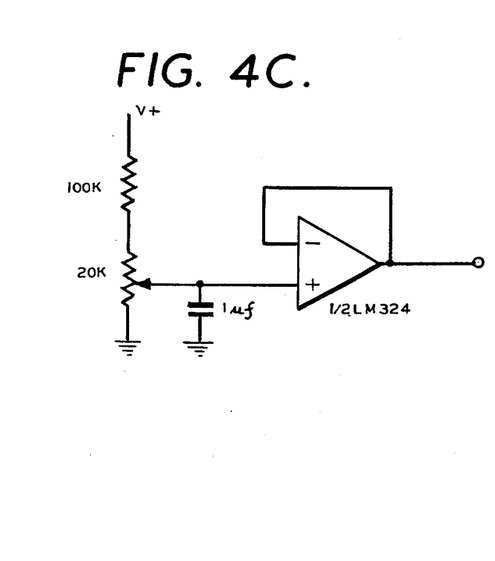
FIG. 4C is a circuit diagram of one embodiment of a voltage reference for use in the apparatus of FIG. 4.

Preferred embodiments of the scaling amplifier, the summing amplifier, and the reference voltage are shown in FIGS. 4A, 4B, and 4C respectively. Since these circuits are of conventional design, a detailed description of their construction and mode of operation is deemed unnecessary. Numerous variations in the circuitry will readily suggest themselves to persons or ordinary skill and are within the intended scope of this invention.

It may also be useful to record the data from the chest and the abdomen on a magnetic tape recorder for later analysis, placing it in series where shown as a dashed box in FIG. 4. Any suitable unit might be used, for example, a four channel portable Oxford Medilog Cassette Recorder, which both records and plays back a number of channels of information.

The use of a portable tape recorder permits long-term data accumulation on the respiration of ambulatory patients, since all of the apparatus up to and including such a recorder can be made small, light and unobtrusive to the patient. Alternatively, radio telemetry may be used to couple the vests and related apparatus on the patient to fixed monitoring and recording equipment.

Another option is to place a preprocessor unit immediately following the scaling amplifiers. Preprocessor here means, simply, a circuit which does some simple calculation using the respiration signals. These calculations may be done manually from the recorded data, but it might be useful to a clinical physician to have the calculation results continuously, in real time, while the patient breathes. Having the respiration signals in electronic form as provided by the present invention makes this possible, with the use of standard circuits known to one skilled in the art. With such circuits, various types of analyses can be made on the signals such as minute volume, respiration rate, maximal voluntary ventilation and detection of obstructive and central apneas.

Apnea refers simply to a cessation of breathing, and there are two kinds. One is the obstructive apnea, caused as the name indicates by some sort of blockage of the windpipe, or of both mouth and nose. Obstructive apneas are characterized by out of phase excursion of the chest and abdominal excursions with a consequent reduction in summed breathing volume, all of which are measured and displayed by the apparatus of the present invention. The other apnea is the central apnea, in which the patient ceases any and all efforts to breathe. Central apneas are distinguished by cessation of both rib cage and abdominal movement.

Other results which may either be calculated manually from the recorded data, or obtained by a standard circuit, include time taken for inspiration, time taken for expiration, the ratio between these times, or the phase difference between chest excursion and abdominal excursion. Comparisons could be made with other sources of data, for example, heart monitors. Finally, it might prove useful to use an analog to digital converter circuit, well known in the art, in order to supply the chest and abdomen signals directly to a computer. Any of these standard circuits could be placed where the preprocessor is indicated on FIG. 4 by a dashed box.

Various other arrangements of magnetic and graphic recorders, digital voltmeters, and preprocessors, singly and in combination, will be apparent to one skilled in the art, and may be made to satisfy particular needs.

Calibration of the apparatus will now be described. Referring to FIG. 4, the scaling amplifiers must be set for each patient so that the output of the summing amplifier will always represent the same respiration volume as that measured directly by a spirometer. This may be done by trial and error as the patient assumes various body positions with both the spirometer and the inventive apparatus connected. It is faster and more convenient for the patient, however, to use the procedure which follows. Only a few breaths are needed in each of two positions, after which the spirometer can be removed. Very little cooperation from the patient is required, and, indeed, the calibration can be carried out with a critically ill or even an unconscious patient. The two body positions required may be, in such a case, supine on a bed or stretcher with the head end raised, and supine with, instead, the foot end raised. Standing and prone positions are used in the example below, but any pair of positions may be used so long as they differ in the relative chest and abdomen breathing contributions. Usually, the difference comes from shifting the weight between chest and abdomen.

The calibration procedure is:

(1) Adjust the spirometer scaling amplifier so that the signal during quiet breathing is of an appropriate magnitude for the display, for example, the graphic recorder.

(2) With the reference voltage switched in, set the respective scaling amplifiers for chest and abdomen so that the graphic recorder registers unity for each. Switch out the reference voltage.

(3) Place the patient in one position, for example, standing, and while he breaths quietly obtain a simultaneous set of numerical readings on the graphic recorder for the spirometer ($V_{ss}$), the chest ($C_s$), and the abdomen ($A_s$).

(4) Repeat step (3) with the patient in a different position, for example, prone, obtaining another set of numerical readings ($V_{sp}$, $C_p$, and $A_p$).

(5) Find proportionality constants $K_1$ and $K_2$ so that the following equation for volume of respiration $$V_s = K_1 C + K_2 A$$

can be written. One set of numerical values $V_{ss}$, $C_s$, and $A_s$ for the standing position can be inserted and a second set of numerical values $V_{sp}$, $C_p$, and $A_p$ for the prone position can be inserted, which will result in two equations with only the two unknowns, constant $K_1$ and $K_2$. These may be calculated from $$K_1 = \frac{A_p V_{ss} - A_s V_{sp}}{C_s A_p - C_p A_s}$$

$$K_2 = \frac{C_p V_{ss} - C_s V_{sp}}{C_p A_s - C_s A_p}$$

by longhand, or by using a programmable calculator.

(6) Now once more switch in the reference voltage as in step (2), and reset the respective scaling amplifiers for chest and abdomen so that the graphic recorder registers the calculated number $K_1$ for the chest and the calculated number $K_2$ for the abdomen. Switch out the reference voltage. Calibration is then complete, for this patient, in any position. That is, the output of the summing amplifier will give the same reading on the display as would the spirometer. The spirometer need only be used during the calibration and may now be discarded insofar as this patient is concerned.

It is apparent that the purposes of monitoring the breathing of a critically ill patient will often include the warning that this monitoring will give to the observer that there are lift threatening breathing irregularities, which require immediate medical intervention. The preprocessor may include circuitry to provide an audible or visual alarm when certain irregularities occur, to insure that the observer takes notice.

It is also possible that less elaborate versions of the present invention may prove useful in non-hospital situations. There are situations for which a single elastically deformable tube and conductive loop, rather than two, would be sufficient, and for which calibration before use would be unimportant. The electronic circuitry could also be simplified and abbreviated. For example, if there were fear of possible crib death of an infant, the so-called Sudden Infant Death Syndrome, a simple version of this invention could alert the parents elsewhere in the house, should the infant cease to breath for some set period, perhaps 20 seconds. Alternatively, a bank teller fitted with a similar apparatus could give a "silent alarm" of foul play by simply holding his breath for a brief period. In this latter alternative, the apparatus may include a radio transmitter to give the teller full mobility. This version could also prove useful for use by night watchmen.

Other applications of this invention are (a) monitoring animal respiration in veterinary medicine or scientific studies; (b) measuring changes in area of human or animal body portions other than the torso in respiration; and (c) measuring changes in areas of non-magnetic objects which are not portions of living bodies This last application may for example, include indicating the contained liquid volume in a plastic pouch, or gas volume in such a pouch.

It will be understood that various modifications and alternate configurations may be made in the preferred embodiments shown and described herein without departure from the scope of the invention, and that the invention embraces all such changes, modifications and equivalents as are within the scope of the following claims.

What is claimed is:

1. A method for monitoring respiration in a subject comprising looping an extensible electrical conductor about the subject's torso; holding said conductor in close encircling relation with said torso during respiration; and measuring the inductance of said conductor, said measured inductance providing an indication of said subject's respiration.

2. The method according to claim 1, wherein said looping step comprises looping said conductor about said subject's rib cage and abdomen.

3. The method according to claim 1, further comprising displaying a signal indicative of said measured inductance.

4. The method according to claim 1, wherein said conductor substantially completely encircles said subject's torso.

5. Apparatus for monitoring respiration in a subject comprising:
   an extensible electrical conductor;
   means for supporting said conductor in close encircling relation with said subject's torso during respiration;
   means for measuring the inductance of said conductor; and
   means for correlating said measured inductance with said subject's respiration.

6. The apparatus according to claim 5, wherein said means for measuring the inductance of said conductor comprises a variable frequency LC oscillator employing as inductance said conductor, and a frequency-to-voltage converter in series therewith.

7. The apparatus according to claim 5, wherein said supporting means comprises elastically deformable means for disposition about said subject's torso in elastically deformed condition for self-biasing said elastically deformable means into close encircling relation with said torso; and means for mounting said conductor on said elastically deformable means.

8. The apparatus according to claim 5, further comprising means for displaying a signal indicative of said measured inductance.

9. The apparatus according to claim 5, wherein said means for supporting said conductor in close encircling relation with said subject's torso comprises means for supporting said conductor for substantially fully encircling said subject's torso.

10. A method for monitoring respiration in a subject comprising:
  looping a first extensible electrical conductor about said subject's rib cage;
  looping a second extensible conductor about said subject's abdomen;
  holding said first and second conductors in close encircling relation about said torso during respiration; and
  separately measuring the inductances of each of said conductors during respiration, said measured inductances being indicative of said subject's respiration.

11. The method according to claim 10, further comprising the step of weighting said measured inductances to reflect the different contributions from said first and second torso portions to said subject's respiration volume.

12. The method according to claim 10, further comprising the step of displaying signals indicative of said measured inductances.

13. The method according to claim 10, wherein said step of looping said first extensible conductor about said subject's rib cage comprises looping said first conductor substantially completely about said subject's rib cage, and wherein said step of looping said second extensible conductor about said subject's abdomen comprises looping said second conductor substantially completely about said subject's abdomen.

14. Apparatus for monitoring respiration in a subject comprising;
  a first extensible electrical conductor adapted to be extended circumferentially about said subject's rib cage;
  a second extensible electrical conductor adapted to be extended circumferentially about said subject's abdomen;
  means for supporting said conductors in close encircling relation about said subject during respiration;
  means for separately measuring the inductances of said conductors; and
  means for correlating said measured inductances with said subject's respiration.

15. The apparatus of claim 14, wherein said means for measuring said inductances of said first and second conductors comprises, for each conductor, a variable frequency LC oscillator employing as inductance the corresponding conductor, and a frequency-to-voltage converter, said variable frequency LC oscillator being connected in series with said frequency-to-voltage converter.

16. The apparatus according to claim 14, further comprising means for weighting said measured inductances to reflect the different contributions from said rib cage and abdomen to said subject's respiration volume.

17. The apparatus according to claim 16, wherein said weighting means comprises scaling amplifiers.

18. The apparatus according to claim 14, wherein said supporting means comprises elastically deformable means for disposition about said rib cage and abdomen in elastically deformed condition for self-biasing said elastically deformable means into close encircling relation with said torso; and means for mounting said first and second conductors on said elastically deformable means.

19. The apparatus according to claim 14, further comprising means for displaying signals indicative of said measured inductances.

20. The apparatus according to claim 14, wherein said means for supporting said conductors in close encircling relation about said subject's rib cage and abdomen comprises means for supporting said conductors for substantially fully encircling said subject's rib cage and abdomen.

* * * * *